United States Patent
Wieslander et al.

(10) Patent No.: US 12,144,790 B2
(45) Date of Patent: Nov. 19, 2024

(54) DIALYSIS CONCENTRATE

(71) Applicant: GAMBRO LUNDIA AB, Lund (SE)

(72) Inventors: Anders Wieslander, Lund (SE); Ola Carlsson, Lund (SE); Karin Sandin, Sodra Sandby (SE); Simon Enarsson, Lund (SE); Viktoria Hancock, Eslov (SE)

(73) Assignee: Gambro Lundia AB, Lund (SE)

( * ) Notice: Subject to any disclaimer, the term of this patent is extended or adjusted under 35 U.S.C. 154(b) by 1090 days.

(21) Appl. No.: 16/095,094

(22) PCT Filed: May 5, 2017

(86) PCT No.: PCT/EP2017/060771
§ 371 (c)(1),
(2) Date: Oct. 19, 2018

(87) PCT Pub. No.: WO2017/191302
PCT Pub. Date: Nov. 9, 2017

(65) Prior Publication Data
US 2019/0151265 A1    May 23, 2019

(30) Foreign Application Priority Data
May 6, 2016    (SE) .................................. 1650612-3

(51) Int. Cl.
| | |
|---|---|
| *A61K 31/19* | (2006.01) |
| *A61K 9/08* | (2006.01) |
| *A61K 9/50* | (2006.01) |
| *A61K 31/7004* | (2006.01) |
| *A61K 33/06* | (2006.01) |
| *A61K 33/14* | (2006.01) |
| *A61K 33/26* | (2006.01) |
| *A61K 47/02* | (2006.01) |
| *A61M 1/16* | (2006.01) |
| *A61M 1/28* | (2006.01) |

(52) U.S. Cl.
CPC ................ *A61K 31/19* (2013.01); *A61K 9/08* (2013.01); *A61K 9/5036* (2013.01); *A61K 31/7004* (2013.01); *A61K 33/06* (2013.01); *A61K 33/14* (2013.01); *A61K 33/26* (2013.01); *A61K 47/02* (2013.01); *A61M 1/1654* (2013.01); *A61M 1/287* (2013.01)

(58) Field of Classification Search
CPC ................ A61K 2300/00; A61K 31/19; A61K 31/7004; A61K 33/06; A61K 33/14; A61K 33/26; A61K 47/02; A61K 9/08; A61K 9/5036; A61M 1/1654; A61M 1/287
See application file for complete search history.

(56) References Cited

U.S. PATENT DOCUMENTS

| | | | |
|---|---|---|---|
| 5,344,392 | A | 9/1994 | Senninger |
| 5,827,820 | A | 10/1998 | duMoulin |
| 6,020,007 | A | 2/2000 | Veech |
| 6,610,206 | B1 | 8/2003 | Callan |
| 6,689,393 | B1 | 2/2004 | Knerr |
| 2005/0020507 | A1 | 1/2005 | Zieske |
| 2005/0276868 | A1 | 12/2005 | DeGreve |
| 2017/0281845 | A1* | 10/2017 | Manda ...................... C02F 1/42 |

FOREIGN PATENT DOCUMENTS

| | | |
|---|---|---|
| EP | 1008341 | 6/2000 |
| EP | 2965747 | 1/2016 |
| JP | H05-502614 | 5/1993 |
| JP | 2006-000482 | 1/2006 |
| JP | 2015-218141 | 12/2015 |
| WO | WO 92/05814 | 4/1992 |
| WO | WO 01/19413 | 3/2001 |
| WO | WO 2004/105730 | 12/2004 |
| WO | WO 2005/011631 | 2/2005 |
| WO | WO 2006/083653 | 8/2006 |
| WO | WO 2012/129501 | 9/2012 |
| WO | WO 2013/141896 | 9/2013 |

OTHER PUBLICATIONS

PCT Search Report and Written Opinion for PCT/EP2017/060769 dated Jul. 18, 2017 (15 pages).

(Continued)

*Primary Examiner* — James H Alstrum-Acevedo
*Assistant Examiner* — Erinne R Dabkowski
(74) *Attorney, Agent, or Firm* — Mueting Raasch Group

(57) ABSTRACT

The invention provides a first concentrate comprising lactate and calcium ions, said first concentrate having increased stability against precipitation at temperatures around +4° C., said first concentrate being useful for preparing a ready-to-use dialysis fluid by mixing said first concentrate with water and optionally a second concentrate comprising glucose, wherein that the lactate concentration $L_{conc}$ (expressed in moles per litre, M) of the concentrate fulfills the conditions: a) $L_{conc} > 0.8$ M; and b) $L_{conc} < (1.9 - 0.4 \times Ca_{ready})$ M; and wherein $Ca_{ready}$ is the calcium concentration of the ready-to-use dialysis fluid expressed in millimoles per litre (mM).

19 Claims, 2 Drawing Sheets

(56) References Cited

OTHER PUBLICATIONS

PCT Search Report and Written Opinion for PCT/EP2017/060771 dated Aug. 7, 2017 (10 pages).
Himmele et al., "A New Neutral-pH Low-GDP Peritoneal Dialysis Fluid", *Peritoneal Dialysis International*, vol. 32, No. 4, pp. 444-452, Mar. 2012.
Erixon et al., "How to Avoid Glucose Degradation Products in Peritoneal Dialysis Fluids", *Peritoneal Dialysis International*, vol. 26, pp. 490-497, Jul. 2006.
Office Action issued in Europe for Application No. 17722016.7-1109 dated Oct. 14, 2022 (8 pages).

\* cited by examiner

DIALYSIS CONCENTRATE

This application is a U.S. National Stage Application of International Application No. PCT/EP2017/060771, filed 5 May 2017 and published in English on 9 Nov. 2017 as International Publication No. WO 2017/191302 A1, which claims the benefit of priority under 35 U.S.C. § 119 (a) of Swedish Patent Application No. 1650612-3 filed 6 May 2016, each of which are incorporated herein by reference in their entireties.

The present invention relates to the field of medical treatments. More specifically, the present invention relates to solutions used for dialysis therapy. In particular, the present invention relates to a first concentrate that could be used for preparing a ready-to-use dialysis fluid after mixing with purified and/or sterilized water and/or one or more further concentrates. The invention also relates to a kit comprising at least a first and a second concentrate for preparing a ready-to-use dialysis fluid, wherein the ready-to-use dialysis fluid is prepared by mixing the at least first and second concentrate with optionally purified water.

BACKGROUND OF THE INVENTION

Due to disease, insult or other causes, a person's renal system can fail. In renal failure of any cause, there are several physiological derangements. The balance of water, minerals, and the excretion of daily metabolic load are no longer possible in renal failure. During renal failure, toxic end products of nitrogen metabolism (e.g., urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney function is critical to many people because the treatment is life-saving.

Hemodialysis, hemofiltration and peritoneal dialysis are three types of dialysis therapies generally used to treat loss of kidney function. Hemodialysis treatment removes waste, toxins and excess water directly from the patient's blood. The patient is connected to a hemodialysis machine and the patient's blood is pumped through the machine. For example, needles or catheters can be inserted into the patient's veins and arteries to connect the blood flow to and from the dialysis machine. As blood passes through a dialyzer in the hemodialysis machine, the dialyzer removes the waste, toxins and excess water from the patient's blood and returns the blood to infuse back into the patient. A large amount of dialysis fluid, for example about 90-120 liters, is used by most hemodialysis machines to dialyze the blood during a single hemodialysis therapy. The spent dialysis fluid or dialysate is then discarded. Hemodialysis treatment lasts several hours and is generally performed in a treatment center about three times per week.

Hemofiltration is a convection-based blood cleansing technique. Blood access can be venovenous or arteriovenous. As blood flows through the hemofilter, a transmembrane pressure gradient between the blood compartment and the ultrafiltrate compartment causes plasma water to be filtered across the highly permeable membrane. As the water crosses the membrane, it convects small and large molecules across the membrane and thus cleanses the blood. An excessive amount of plasma water is eliminated by filtration. Therefore, in order to keep the body water balanced, fluid must be substituted continuously by a balanced electrolyte solution (replacement or substitution fluid) infused intravenously. This substitution fluid can be infused either into the arterial blood line leading to the hemofilter (predilution) or into the venous blood line leaving the hemofilter (postdilution).

Peritoneal dialysis utilizes a sterile dialysis fluid, which is infused into a patient's peritoneal cavity and into contact with the patient's peritoneal membrane. Waste, toxins and excess water pass from the patient's blood stream through the peritoneal membrane and into the dialysate. The transfer of waste, toxins and excess water from the bloodstream into the dialysate occurs due to diffusion and convection during a dwell period. The convective transport is due to that an osmotic agent in the dialysate creates an osmotic gradient across the membrane. The dialysate is later drained from the patient's peritoneal cavity to remove the waste, toxins and excess water from the patient.

There are various types of peritoneal dialysis therapies, including continuous ambulatory peritoneal dialysis ("CAPD") and automated peritoneal dialysis (APD). CAPD is a manual dialysis treatment, in which the patient connects the catheter to a bag of fresh dialysis fluid and allows the dialysis fluid to dwell within the cavity to transfer waste, toxins and excess water from the patient's blood stream to the dialysis fluid. After a dwell period, the patient drains the dialysate and then repeats the manual dialysis procedure. Tubing sets with "Y" connectors for the solution and drain bags are available that can reduce the number of connections the patient must make. The tubing sets can include pre-attached bags including, for example, an empty bag and a bag filled with the dialysis fluid.

In CAPD, the patient performs several drain, fill and dwell cycles during the day, for example, about four times per day. Each treatment cycle, which includes a drain, fill and dwell, takes about four to twelve hours.

APD is similar to CAPD in that the dialysis treatment includes a drain, fill, and dwell cycle. However, a dialysis machine automatically performs three or more cycles of peritoneal dialysis treatment, typically overnight while the patient sleeps.

With automated peritoneal dialysis, an automated dialysis machine fluidly connects to an implanted catheter. The automated dialysis machine also fluidly connects to a source or bag of fresh dialysis fluid and to a fluid drain. The dialysis machine pumps dialysate from the peritoneal cavity, through the catheter, to the drain. The dialysis machine then pumps fresh dialysis fluid from the dialysis fluid source, through the catheter, and into the patient's peritoneal cavity. The automated machine allows the dialysis fluid to dwell within the cavity so that the transfer of waste, toxins and excess water from the patient's blood stream may occur. A computer controls the automated dialysis machine so that the dialysis treatment occurs automatically when the patient is connected to the dialysis machine, for example when the patient sleeps. That is, the dialysis system automatically and sequentially fills the peritoneal cavity with dialysis fluid, pumps dialysate out of the peritoneal cavity, and repeats the procedure.

Several drain, fill, and dwell cycles will occur during treatment. Also, a final volume "last fill" is typically used at the end of the automated dialysis treatment, which remains in the peritoneal cavity of the patient when the patient disconnects from the dialysis machine for the day. Automated peritoneal dialysis frees the patient from having to manually perform the drain, dwell and fill steps during the day.

In general, standard peritoneal dialysis fluids contain glucose at a concentration of 1.5%-4.25% by weight to effect transport of water and metabolic waste across the peritoneal membrane. Glucose is generally recognized as a safe and effective osmotic agent, particularly for short dwell exchanges. Glucose-based peritoneal dialysis solutions are typically formulated at a pH of 5.0 to 5.5. This is to avoid discomfort and/or pain during infusion without excessive degradation of glucose.

However, at this pH glucose can undergo significant degradation, thus resulting in a number of reaction products commonly referred to as glucose degradation products ("GDPs"). The GDPs may induce major problems in connection with peritoneal dialysis treatment. In order to avoid these and other problems, it has been proposed in WO2005/011631 to formulate peritoneal dialysis solutions into at least two separate solution parts. A first part includes a glucose concentrate and a second part includes a buffer concentrate. The first and second parts are separately sterilized at an acidic pH and then admixed prior to use, such as infusion into a patient during peritoneal dialysis. A dialysis fluid prepared by admixing two such solution parts has enhanced biocompatible characteristics such as reduced levels of glucose degradation products.

Patients on automated peritoneal dialysis typically perform 4-10 dialysis cycles at night and up to 2 cycles during the day. The fill volume per cycle depends on body size and type of treatment but amounts typically to 0.5-3.0 liters per cycle. A typical consumption could therefore be within the range of 8-17 liters per 24 hours. In order to reduce transportation costs, and environmental impact and facilitate handling of solution containers, it has been suggested to produce concentrates based on the two solution parts disclosed in WO 2005/011631. However, it turns out that such concentrates could be unstable and that dissolved constituents sometimes precipitate during storage, and especially during storage at low temperatures (around +4° C.) of concentrates comprising lactate and calcium. It is necessary that medical preparations are stable and that patients may use them with a minimum of risk. Accordingly, there is a need for stable and concentrated solutions that can be used for preparing ready-to-use dialysis fluid after dilution and admixture.

SUMMARY OF THE INVENTION

The present invention solves this problem by providing a first concentrate having increased stability against precipitation when stored at temperatures from +4° C. to +40° C.

In a first embodiment, the present invention provides an aqueous first concentrate comprising lactate and calcium ions, said first concentrate having increased stability against precipitation at temperatures around +4° C. The first concentrate is useful for preparing a ready-to-use dialysis fluid by mixing said first concentrate with water and optionally a second concentrate comprising glucose. The lactate concentration $L_{conc}$ (expressed in moles per litre, M) of the first concentrate fulfills the conditions:

a) $L_{conc} > 0.75$ M; and
b) $L_{conc} < (1.9 - 0.4 \times Ca_{ready})$ M; and wherein $Ca_{ready}$ is the calcium concentration of the ready-to-use dialysis fluid expressed in millimoles per litre (mM).

In a preferred embodiment, the first concentrate also fulfills the condition c) $L_{conce} < (1.7 - 0.4 \times Ca_{ready})$ M wherein $Ca_{ready}$ has the same meaning as above.

In a preferred embodiment, the first concentrate also fulfills the condition $L_{conc} > 0.80$ M.

In a preferred embodiment, the ratio $R = L_{conc}/Ca_{conc}$ is within the range of 20-40, wherein $Ca_{conc}$ is the calcium concentration of the first concentrate expressed in moles per liter (M).

In a more preferred embodiment the ratio R is within the range of 22-33.

In a preferred embodiment, the first concentrate has a pH within the range of 5.5-9.0.

In a more preferred embodiment, the first concentrate has a pH within the range of 6.5-8.0.

According to another embodiment of the invention, the first concentrate has a pH within the range of 6.0-8.5.

In a preferred embodiment, the first concentrate also comprises ions selected from the group of $Na^+$, $K^+$, $Mg^{2+}$, and $Cl^-$.

In a preferred embodiment, the first concentrate is terminally sterilized.

In a second embodiment, the invention provides a kit of parts for preparing a peritoneal dialysis fluid comprising:
 a first concentrate which is a concentrate composition according to the first aspect of the invention; and
 a second concentrate which is an acidic glucose concentrate.

In a preferred embodiment, the second concentrate has a pH within the range of 1.5-4.

In a more preferred embodiment, the second concentrate has a pH within 2.0-3.2

In a preferred embodiment, the second concentrate has been made acidic by adding hydrochloric acid.

In a preferred embodiment, the second concentrate is a glucose concentrate saturated to a level within the range from 30%-70%.

In a preferred embodiment, said second concentrate is terminally sterilized.

In a third embodiment, the invention provides a multi-chambered bag for storing a kit of parts according to the second aspect, wherein said first concentrate is stored in a first chamber, and said second concentrate is stored in a second chamber.

In a fourth embodiment, the invention provides a method of producing a dialysis solution, the method comprising the steps of:
 i) formulating a first and a second concentrate of the kit of parts according to the second aspect of the invention;
 ii) sterilizing said first and second concentrates;
 ii) providing optionally purified water; and
 iii) mixing appropriate amounts of said sterilized first and second concentrates and mixing them with an appropriate amount of said optionally purified water, thereby obtaining a ready-to-use dialysis fluid.

DETAILED DESCRIPTION OF THE INVENTION

Figure 1:
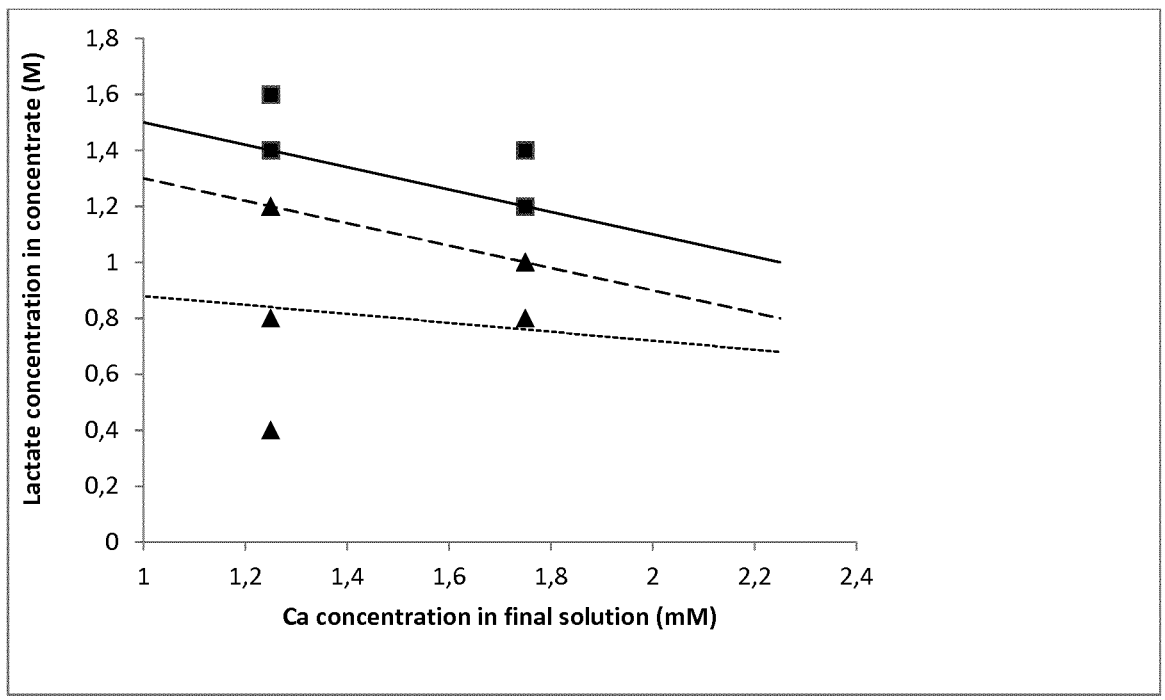
FIG. 1 is a diagram showing lactate concentration in the aqueous first concentrate as a function of the calcium concentration of the final ready-to-use dialysis fluid.

The present invention generally relates to dialysis solutions. In particular, the present invention relates to concentrates for manufacturing ready-to-use dialysis solutions. Such ready-to-use dialysis solutions can be used in a variety of suitable applications. Preferably, the dialysis solutions are used during peritoneal dialysis, such as during automated peritoneal dialysis.

However, it should be appreciated that the present invention can be used in a variety of different and suitable dialysis therapies to treat kidney failure. Dialysis therapy as the term or like terms are used throughout the text is meant to include and encompass any and all suitable forms of therapies that utilizes the patient's blood to remove waste, toxins and excess water from the patient. Such therapies, such as hemodialysis, hemofiltration and hemodiafiltration, include both intermittent therapies and continuous therapies used for continuous renal replacement therapy (CRRT). The continuous therapies include, for example, slow continuous ultrafiltration (SCUF), continuous venovenous hemodiafiltration (CVVH), continuous venovenous hemodialysis (CVVHD), continuous venovenous hemodiafiltration (CCVHDF), continuous arteriovenous hemodialysis (CAVHD), continuous arteriovenous hemofiltration (CAVHDF), continuous ultrafiltration periodic intermittent hemodialysis or the like. Preferably, the dialysis solutions are used during peritoneal dialysis, such as automated peritoneal dialysis, continuous ambulatory peritoneal dialysis, continuous flow peritoneal dialysis and the like. Further, although the present invention, in an embodiment, can be utilized in methods providing dialysis therapy for patients having chronic kidney failure or disease, it shall be appreciated that the present invention can be used for acute dialysis needs, for example in an emergency room setting. Lastly, as one skilled in the art appreciates, the intermittent forms of therapy (i.e., hemofiltration, hemodialysis, peritoneal dialysis, and hemodiafiltration) may be used in the in center, self/limited care as well as the home settings.

Hemodialysis involves withdrawing blood from the body and cleaning it in an extracorporeal blood circuit and then returning the cleansed blood to the body. The extracorporeal blood circuit includes a dialyzer which comprises a semipermeable membrane. The semipermeable membrane has a blood side and a dialysate side, and waste substances and excess fluid are removed from the blood passing on the blood side of the semipermeable membrane through the semipermeable membrane over to the dialysate side of the semipermeable membrane.

Hemodialysis may be performed in three different treatment modes, hemodialysis, hemofiltration, and hemodiafiltration. Common to all three treatment modes is that the patient is connected by a blood line to the dialysis machine, which continuously withdraws blood from the patient. The blood is then brought in contact with the blood side of the semipermeable membrane within the dialyzer in a flowing manner.

In hemodialysis, an aqueous solution called dialysis fluid is brought in contact with the opposite membrane surface, the dialysate side, in a flowing manner. Waste substances (toxins) and solutes are removed/controlled mainly by diffusion. Excess fluid is removed by applying transmembrane pressure over the semipermeable membrane. Solutes and nutrients may diffuse in the opposite direction from the dialysis fluid, through the semipermeable membrane and into the blood.

In hemofiltration, no dialysis fluid is brought in contact with the dialysate side of the semipermeable membrane. Instead only a transmembrane pressure is applied over the semipermeable membrane thereby removing fluid and waste substances, from the blood through the semipermeable membrane wall and into the dialysate side thereof (convective flow). Fluid and waste substances are then passed to drain. To replace some of the removed fluid, a correctly balanced electrolyte/buffer dialysis fluid (also named infusion fluid, replacement fluid, or substitution fluid) is infused into the extracorporeal blood circuit. This infusion may be done either pre the dialyzer (pre-infusion mode) or post the dialyzer (post-infusion mode) or both.

Hemodiafiltration is a combination of hemodialysis and hemofiltration, a treatment mode that combines transport of waste substances and excess fluids through the semipermeable wall by both diffusion and convection. Thus, here a dialysis fluid is brought in contact with the dialysate side of the semipermeable membrane in a continuously flowing manner, and a dialysis fluid (also named infusion fluid or replacement fluid) is used for infusion into the extracorporeal blood circuit in pre-infusion mode, post-infusion mode or both.

For many patients, hemodialysis is performed for 3-5 hours, three times per week. It is usually performed at a dialysis centre, although home dialysis is also possible. When home dialysis is performed patients are free to perform dialysis more frequently and also in more gentle treatments with longer treatment times, i.e. 4-8 hours per treatment and 5-7 treatments per week. The dose and treatment times may be adjusted due to different demand of the patients. In the case of patients suffering from acute renal insufficiency, a continuous treatment, throughout a major portion of the entire day for up to several weeks, a continuous renal replacement therapy (CRRT), or intermittent renal replacement therapy (IRRT) is the indicated treatment depending on the patients' status. Also here the removal of waste substances and excess fluid from the patient is effected by any or a combination of the treatment modes hemodialysis, hemofiltration and hemodiafiltration.

In a peritoneal dialysis treatment a hypertonic dialysis fluid is infused into the peritoneal cavity of the patient. In this treatment solutes and water is exchanged in the capillary vessels of a patient's peritoneal membrane with said hypertonic dialysis fluid. The principle of this method is diffusion of solutes transferred according to the concentration gradient and water migration due to the osmotic differences over the peritoneal membrane.

The dialysis fluids used in all the above dialysis techniques contain mainly electrolytes like sodium, magnesium, calcium, potassium, an acid/base buffer system and optionally glucose or a glucose-like compound. All the components in dialysis fluids are selected to control the levels of electrolytes and the acid-base equilibrium within the blood and to remove waste materials from the blood.

The daily consumption of dialysis fluids for patients on automated peritoneal dialysis is much lower than for patients on hemodialysis, but it is still quite large. Typically, a patient on automated peritoneal dialysis consumes about 12-15 liters of dialysis fluid each treatment session. Such a large consumption creates a lot of problems. Firstly, it is neither easy nor convenient for the patients or their care givers to carry around heavy containers of dialysis liquids. Secondly it is quite expensive to transport and distribute these heavy containers from manufactures or distributors to patients and clinics. Hence, there is a clear incentive to find ways of facilitating handling by patients and care givers as well as reducing the transportation need.

One way of facilitating handling as well as reducing the need for transportation is to develop concentrates which can be diluted with optionally purified and/or sterilized water in order to produce a reconstituted ready-to-use dialysis fluid. Suitable containers for such concentrates are much smaller, less heavy, and consequently easier to handle. As a concentrate lasts much longer compared to an equivalent amount of a ready-to-use solution, the transportation need is also reduced. The environmental impact of manufacturing as well as transporting concentrates is also reduced.

It is important that such concentrates are stable at all reasonable storage temperatures, such as from +4° C. to +40° C. In particular, it is important that no precipitations are formed at such storage conditions. In concentrates comprising both lactate as well as calcium ions, there is a risk that precipitations are formed, especially at temperatures close to +4° C. and at high lactate and calcium ion concentrations. It has, however, turned out that it is possible to mathematically express whether precipitations will form in a particular concentrate.

Accordingly, a stable first concentrate comprising both lactate and calcium ions has been obtained if the lactate concentration $L_{conc}$ (expressed in moles per litre, M) of the concentrate fulfills the conditions:

a) $L_{conc} > 0.75$ M; and
b) $L_{conc} < (1.9 - 0.4 \times Ca_{ready})$ M; and wherein $Ca_{ready}$ is the calcium concentration of the ready-to-use dialysis fluid expressed in millimoles per litre (mM). It is preferred to use slightly more concentrated solutions wherein $L_{conc} > 0.80$ M.

In order to minimize the risk for precipitation, the concentrate composition should also fulfill the condition:

c) $L_{conc} < (1.85 - 0.4 \times Ca_{ready})$ M wherein $Ca_{ready}$ has the same meaning as above. Other similar variants of the equation of condition c) could also be considered, such as $L_{conc} < (1.75 - 0.4 \times Ca_{ready})$ M, $L_{conc} < (1.7 - 0.4 \times Ca_{ready})$ M, $L_{conc} < (1.8 - 0.4 \times Ca_{ready})$ M, and $L_{conc} < (1.65 - 0.4 \times Ca_{ready})$ M.

The stability of different variants of the first concentrate are shown in FIG. 1, where the lactate concentration in the first concentrate is shown as a function of the calcium concentration of the ready-to-use dialysis fluid. In the diagram of FIG. 1, first concentrates in which precipitates were formed are indicated with squares and first concentrates without any precipitation are indicated with triangles. The uppermost curve corresponds to condition b) above and the middle curve corresponds to condition c) above.

The first concentrate of the present invention can include several different components. As already indicated, the first concentrate is buffered by lactate. The buffer pH can include any suitable level effective for formulating and sterilizing the concentrate composition and subsequently formulating a ready-to-use dialysis solution that includes a mixture of the first concentrate, a second concentrate, which is an acidic glucose concentrate and optionally purified water. The pH of the first concentrate should be within the range of 5.5-9.0, and preferably within the range of 6.5-8.0. The first concentrate may contain other electrolytes such as Cl⁻, Na⁺, $Mg^{2+}$, and K⁺ in addition to $Ca^{2+}$. Furthermore, a pH adjusting agent can be added to the first concentrate, such as sodium hydroxide, hydrochloric acid, and/or the like. Typical concentrations of electrolytes are:

| | | |
|---|---|---|
| Sodium chloride | 1.5-3.3 | M |
| Calcium chloride | 0.025-0.0375 | M |
| Magnesium chloride | 0-0.008 | M |

The first concentrate is intended to be used as one component of a kit of parts for preparing a peritoneal dialysis composition. Said kit also comprises a second concentrate, which is an acidic glucose concentrate. In an embodiment, the acidic concentrate has a pH that ranges from 1.5-4.0, preferably from 2.0-3.2. The second concentrate may also include a pH-adjusting agent. Examples of pH adjusting agents include an inorganic acid, such as hydrochloric acid. Typically, the second concentrate is saturated to a level within the range of 30%-70%. The second concentrate may also be terminal sterilized.

The first and second concentrates may be stored in a multi-chambered bag for convenience. Then, the first concentrate is stored in a first chamber and the second concentrate in a second chamber. Such a multi-chambered bag may be equipped with connections and conduits for connecting the chambers to a mixing unit, where the concentrates are mixed and diluted.

The acid glucose concentrate, the concentration composition and the purified water can be formulated, sterilized and admixed in any suitable manner prior to use, such as prior to infusion by peritoneal dialysis. Water should be within limits that are safe from a microbiological and chemical perspective; this water could for example be "purified water", "highly purified water", "ultrapure water", "water for injection" (WFI), "sterile WFI", "water for hemodialysis", "distilled water", "sterile purified water" and "water for pharmaceutical use". In one embodiment, a mixed solution including specific amounts of the first and second concentrates and purified water are formulated into a desired peritoneal dialysis liquid by mixing.

Figure 2:
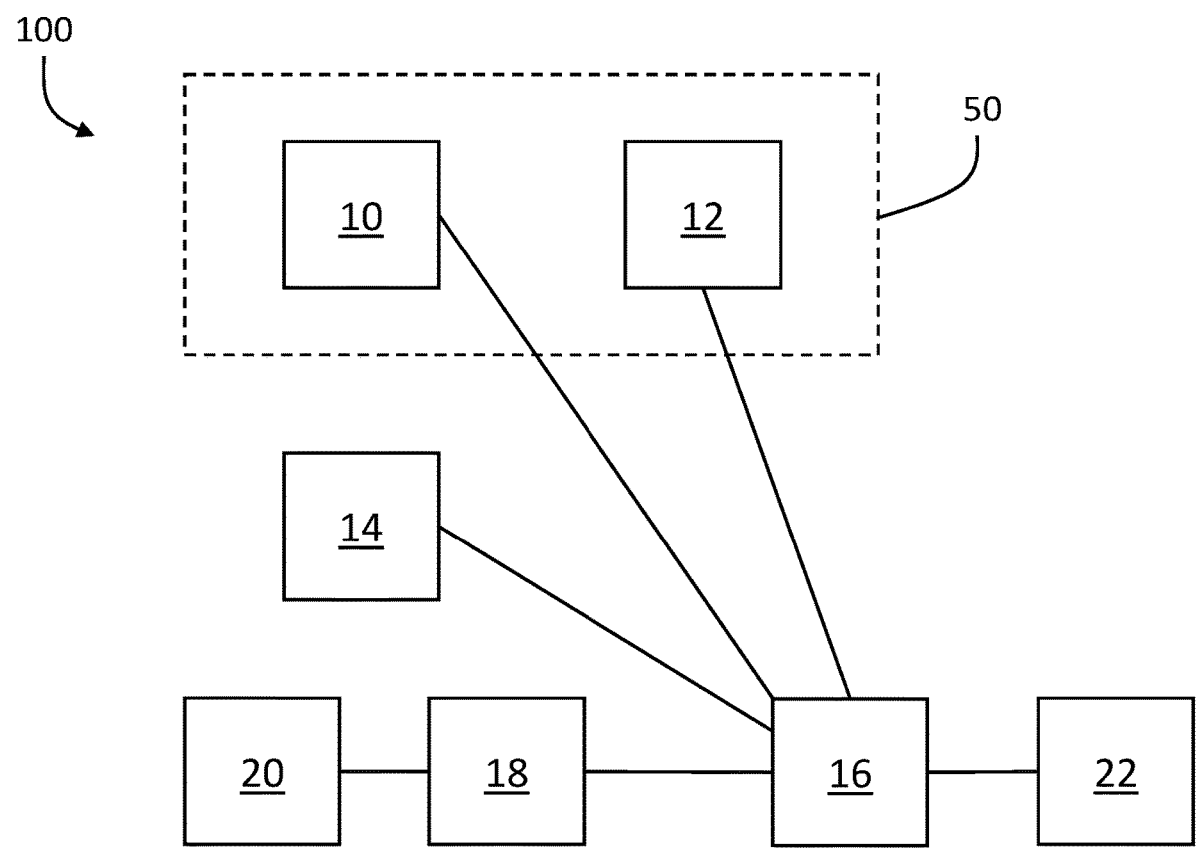
FIG. 2 provides a graphical overview of how to produce a ready-to-use dialysis fluid starting from the kit of parts of the second embodiment of the invention.

FIG. 2 provides a scheme 100 showing one way of how to prepare a desired peritoneal dialysis liquid. A container 10 comprising a first concentrate and a container 12 comprising a second concentrate are each connected to a mixer 16 by conduits. In one embodiment, the containers 10, 12 may be chambers in a multi-chambered bag 50. A source 14 of purified water is also connected to the mixer 16 by a conduit. The mixer 16 is controlled by a controller 18 based on input from a user interface 20. Depending on such user input and control signals from the controller 18, the mixer 16 receives specific amounts of first and optionally second concentrates as well as water from said sources 10, 12, 14, and produces a ready-to-use dialysis fluid that is delivered through output/container 22.

EXAMPLES

Test solutions representing candidate concentrate compositions were prepared by adding different amounts of solid constituents to containers and finally adding purified water up to a desired volume. The test solutions were heat sterilized and incubated for more than two months at +4° C.

A table of ready-to-use dialysis liquids based on the first and second concentrates of each example is also provided at the end of each example.

Example 1

| First concentrate | |
|---|---|
| Sodium chloride | 3.22 M |
| Calcium chloride | 0.06125 M |
| Magnesium chloride | 0.0175 M |
| Sodium lactate | 1.40 M |
| Sodium hydroxide | Ad. pH 6.5-9.0 |

| Second concentrate: 50% glucose | |
|---|---|
| Glucose | 2.775 M |
| Hydrochloric acid | Ad. pH 2.0-3.1 |

| Mixed solution composition example 1 | | | | | |
|---|---|---|---|---|---|
| A (mL/L) | 0 | 30 | 50 | 80 | 100 |
| B (mL/L) | | | 25 | | |
| $Na^+$ (mM) | | | 132 | | |
| $Mg^{2+}$ (mM) | | | 0.50 | | |
| $Ca^{2+}$ (mM) | | | 1.75 | | |
| $Cl^-$ (mM) | | | 97 | | |
| Lactate (mM) | | | 40 | | |
| Glucose (mM) | 0 | 83.3 | 138.8 | 222.0 | 278 |

$Ca_{ready}$ is 1.75 mM for the ready-to-use solution and $L_{conce}$ is 1.40 M for the first concentrate of example 1. Condition a) above is fulfilled as $L_{conc}$ is larger than 0.75 M. Condition b) above is not fulfilled as 1.9−0.4×1.75 mM=1.2, which is less than $L_{conc}$. Precipitations were found in the first concentrate.

Example 2

| First concentrate | |
|---|---|
| Sodium chloride | 3.22 M |
| Calcium chloride | 0.04375 M |
| Magnesium chloride | 0.00875 M |
| Sodium lactate | 1.40 M |
| Sodium hydroxide | Ad. pH 6.5-9.0 |

| Second concentrate: 50% glucose | |
|---|---|
| Glucose | 2.775 M |
| Hydrochloric acid | Ad. pH 2.0-3.1 |

| Mixed solution composition example 2 | | | | | |
|---|---|---|---|---|---|
| A (mL/L) | 0 | 30 | 50 | 80 | 100 |
| B (mL/L) | | | 25 | | |
| $Na^+$ (mM) | | | 132 | | |
| $Mg^{2+}$ (mM) | | | 0.25 | | |
| $Ca^{2+}$ (mM) | | | 1.25 | | |
| $Cl^-$ (mM) | | | 95 | | |
| Lactate (mM) | | | 40 | | |
| Glucose (mM) | 0 | 83.3 | 138.8 | 222.0 | 278 |

$Ca_{ready}$ is 1.25 mM for the ready-to-use solution and $L_{conce}$ is 1.40 M for the first concentrate of example 1. Condition a) above is fulfilled as $L_{conc}$ is larger than 0.75 M. Condition b) above is not fulfilled as 1.9−0.4×1.25 mM=1.4, which is equal to $L_{conc}$. Precipitations were found in the first concentrate.

Example 3

| First concentrate | |
|---|---|
| Sodium chloride | 2.76 M |
| Calcium chloride | 0.0525 M |
| Magnesium chloride | 0.0075 M |
| Sodium lactate | 1.20 M |
| Sodium hydroxide | Ad. pH 6.5-9.0 |

| Second concentrate: 50% glucose | |
|---|---|
| Glucose | 2.775 M |
| Hydrochloric acid | ad pH. 2.0-3.1 |

| Mixed solution composition example 3 | | | | | |
|---|---|---|---|---|---|
| A (mL/L) | 0 | 30 | 50 | 80 | 100 |
| B (mL/L) | | | 33.3 | | |
| $Na^+$ (mM) | | | 132 | | |
| $Mg^{2+}$ (mM) | | | 0.25 | | |
| $Ca^{2+}$ (mM) | | | 1.75 | | |
| $Cl^-$ (mM) | | | 96 | | |
| Lactate (mM) | | | 40 | | |
| Glucose (mM) | 0 | 83.3 | 138.8 | 222.0 | 278 |

$Ca_{ready}$ is 1.75 mM for the ready-to-use solution and $L_{conce}$ is 1.20 M for the first concentrate of example 1. Condition a) above is fulfilled as $L_{conc}$ is larger than 0.75 M. Condition b) above is not fulfilled as 1.9−0.4×1.75 mM=1.2, which is equal to $L_{conc}$. Precipitations were found in the first concentrate.

Example 4

| First concentrate | |
|---|---|
| Sodium chloride | 1.84 M |
| Calcium chloride | 0.035 M |
| Magnesium chloride | 0.005 M |
| Sodium lactate | 0.80 M |
| Sodium hydroxide | Ad. pH 6.5-9.0 |

| Second concentrate: 50% glucose | |
|---|---|
| Glucose | 2.775 M |
| Hydrochloric acid | Ad. pH 2.0-3.1 |

| Mixed solution composition example 4 | | | | | |
|---|---|---|---|---|---|
| A (mL/L) | 0 | 30 | 50 | 80 | 100 |
| B (mL/L) | | | 50 | | |
| $Na^+$ (mM) | | | 132 | | |
| $Mg^{2+}$ (mM) | | | 0.25 | | |
| $Ca^{2+}$ (mM) | | | 1.75 | | |
| $Cl^-$ (mM) | | | 96 | | |
| Lactate (mM) | | | 40 | | |
| Glucose (mM) | 0 | 83.3 | 138.8 | 222.0 | 278 |

$Ca_{ready}$ is 1.75 mM for the ready-to-use solution and $L_{conce}$ is 0.80 M for the first concentrate of example 1. Condition a) above is fulfilled as $L_{conc}$ is larger than 0.75 M.

Condition b) above is fulfilled as 1.9−0.4×1.75 mM=1.2, which is larger than $L_{conc}$. Precipitations were not found in the first concentrate.

Example 5

| First concentrate | |
|---|---|
| Sodium chloride | 1.84 M |
| Calcium chloride | 0.025 M |
| Magnesium chloride | 0.005 M |
| Sodium lactate | 0.80 M |
| Sodium hydroxide | Ad. pH 6.5-9.0 |

| Second concentrate: glucose 50% | |
|---|---|
| Glucose | 2.775 M |
| Hydrochloric acid | Ad. pH 2.0-3.1 |

| Mixed solution composition example 5 | | | | | |
|---|---|---|---|---|---|
| A (mL/L) | 0 | 30 | 50 | 80 | 100 |
| B (mL/L) | | | 50 | | |
| Na+ (mM) | | | 132 | | |
| Mg2+ (mM) | | | 0.25 | | |
| Ca2+ (mM) | | | 1.25 | | |
| Cl− (mM) | | | 96 | | |
| Lactate (mM) | | | 40 | | |
| Glucose (mM) | 0 | 83.3 | 138.8 | 222.0 | 278 |

$Ca_{ready}$ is 1.25 mM for the ready-to-use solution and $L_{conce}$ is 0.80 M for the first concentrate of example 1. Condition a) above is fulfilled as $L_{conc}$ is larger than 0.75 M. Condition b) above is fulfilled as 1.9−0.4×1.25 mM=1.4, which is larger than $L_{conc}$. Precipitations were not found in the first concentrate.

Example 6

| First concentrate | |
|---|---|
| Sodium chloride | 2.76 M |
| Calcium chloride | 0.0375 M |
| Magnesium chloride | 0.0075 M |
| Sodium lactate | 1.20 M |
| Sodium hydroxide | Ad. pH 6.5-9.0 |

| Second concentrate: 50% glucose | |
|---|---|
| Glucose | 2.775 M |
| Hydrochloric acid | Ad. pH 2.0-3.1 |

| Mixed solution composition example 6 | | | | | |
|---|---|---|---|---|---|
| A (mL/L) | 0 | 30 | 50 | 80 | 100 |
| B (mL/L) | | | 33.3 | | |
| Na+ (mM) | | | 132 | | |
| Mg2+ (mM) | | | 0.25 | | |
| Ca2+ (mM) | | | 1.25 | | |
| Cl− (mM) | | | 96 | | |
| Lactate (mM) | | | 40 | | |
| Glucose (mM) | 0 | 83.3 | 138.8 | 222.0 | 278 |

$Ca_{ready}$ is 1.25 mM for the ready-to-use solution and $L_{conce}$ is 1.20 M for the first concentrate of example 1. Condition a) above is fulfilled as $L_{conc}$ is larger than 0.75 M. Condition b) above is fulfilled as 1.9−0.4×1.25 mM=1.4, which is larger than $L_{conc}$. Precipitations were not found in the first concentrate.

Example 7

| First concentrate | |
|---|---|
| Sodium chloride | 2.3 M |
| Calcium chloride | 0.04375 M |
| Magnesium chloride | 0.00625 M |
| Sodium lactate | 1.00 M |
| Sodium hydroxide | ad. pH 6.5-9.0 |

| Second concentrate: 50% glucose | |
|---|---|
| Glucose | 2.775 M |
| Hydrochloric acid | Ad. pH 2.0-3.1 |

| Mixed solution composition example 3 | | | | | |
|---|---|---|---|---|---|
| A (mL/L) | 0 | 30 | 50 | 80 | 100 |
| B (mL/L) | | | 40 | | |
| Na+ (mM) | | | 132 | | |
| Mg2+ (mM) | | | 0.25 | | |
| Ca2+ (mM) | | | 1.75 | | |
| Cl− (mM) | | | 96 | | |
| Lactate (mM) | | | 40 | | |
| Glucose (mM) | 0 | 83.3 | 138.8 | 222.0 | 278 |

$Ca_{ready}$ is 1.75 mM for the ready-to-use solution and $L_{conce}$ is 1.00 M for the first concentrate of example 1. Condition a) above is fulfilled as $L_{conc}$ is larger than 0.75 M. Condition b) above is fulfilled as 1.9−0.4×1.75 mM=1.2, which is larger than $L_{conc}$. Precipitations were not found in the first concentrate.

While the invention has been described in connection with what is presently considered to be the most practical embodiments, it is to be understood that the invention is not to be limited to the disclosed embodiments, but on the contrary, it is intended to cover various modifications and equivalents included within the spirit and scope of the appended claims.

The invention claimed is:

1. A first concentrate comprising lactate and calcium ions, said first concentrate having increased stability against precipitation at temperatures around +4° C., wherein the first concentrate has a lactate concentration $L_{conc}$ expressed in moles per litre (M), wherein 1.5 M > $L_{conc}$ > 0.75 M;

$L_{conc}$ < (1.9−0.4×$Ca_{ready}$) M; and ratio R = $L_{conc}/Ca_{conc}$ is within a range of 20-40, wherein $Ca_{ready}$ is a calcium concentration when the first concentrate is diluted from 1:20 to 1:30 with water and ranges from 1.0 to 2.2 millimoles per litre (mM), and wherein $Ca_{conc}$ is a calcium concentration of the first concentrate expressed in moles per liter (M).

2. The first concentrate according to claim 1, which also fulfills the condition:

$L_{conc} < (1.85 - 0.4 \times Ca_{ready})$ M, wherein $Ca_{ready}$ has the same meaning as in claim 1.

3. The first concentrate according to claim 1, wherein $L_{conc} > 0.80$ M.

4. The first concentrate according to claim 1, wherein the ratio R is within a range of 22-33.

5. The first concentrate according to claim 1, which has a pH within a range of 5.5-9.0.

6. The first concentrate according to claim 5, which has a pH within a range of 6.5-8.0.

7. The first concentrate according to claim 1, wherein the first concentrate also comprises ions selected from the group of $Na^+$, $K^+$, $Mg^{2+}$, and $Cl^-$.

8. The first concentrate according to claim 1, which is terminally sterilized.

9. A kit of parts for preparing a peritoneal dialysis fluid comprising:
a first concentrate according to claim 1; and
a second concentrate which is an acidic glucose concentrate.

10. The kit of parts according to claim 9, wherein the second concentrate has a pH within a range of 1.5-4.

11. The kit of parts according to claim 10, wherein the second concentrate has a pH within 2.0-3.2.

12. The kit of parts according to claim 9, wherein the second concentrate has been made acidic by adding hydrochloric acid.

13. The kit of parts according to claim 9, where the second concentrate is a glucose concentrate saturated to a level within a range from 30%-70%.

14. The kit of parts according to claim 9, wherein said second concentrate is terminally sterilized.

15. A kit for preparing a peritoneal dialysis fluid, the kit comprising:
a first concentrate comprising lactate at a lactate concentration $L_{conc}$ and calcium ions at a calcium ion concentration $Ca_{conc}$, wherein a ratio $R=L_{conc}/Ca_{conc}$ is within a range of 20-40; and
a second concentrate comprising 30% to 70% glucose and having a pH of 1.5-4,
the lactate concentration and the calcium ion concentration being selected such that when the first and second concentrates are mixed with water to produce the peritoneal dialysis fluid having a final calcium ion concentration $Ca_{ready}$, wherein the lactate concentration $L_{conc}$ of the first concentrate is greater than 0.75 M and less than 1.5 M and when the first concentrate is diluted from 1:20 to 1:30 with water, $L_{conc}$ is less than $(1.9 - 0.4 \times Ca_{ready})$ M, where when the first concentrate is diluted from 1:20 to 1:40 with water and $Ca_{ready}$ ranges from 1.0 to 2.2 millimoles per litre.

16. A multi-chambered bag for storing the kit of parts according to claim 9, wherein said first concentrate is stored in a first chamber and said second concentrate is stored in a second chamber.

17. A method of producing a dialysis solution, the method comprising:
formulating a first concentrate and a second concentrate of the kit of parts according to claim 9;
sterilizing said first and second concentrates by heat;
mixing first and second amounts of said sterilized first and second concentrates to form a concentrate mixture, and mixing the concentrate mixture with water, thereby obtaining a ready-to-use dialysis fluid.

18. A method of making a dialysis solution, the method comprising:
mixing a first amount of a first concentrate and a second amount of a second concentrate with water to obtain the dialysis solution,
the first concentrate comprising lactate at a lactate concentration $L_{conc}$ and calcium ions at a calcium ion concentration $Ca_{conc}$, wherein a ratio $R=L_{conc}/Ca_{conc}$ is within a range of 20-40, the second concentrate comprising 30% to 70% glucose and having a pH of 1.5-4, and the dialysis solution comprising calcium at a concentration $Ca_{ready}$,
wherein the lactate concentration $L_{conc}$ of the first concentrate is greater than 0.75 M and less than 1.5 M and when the first concentrate is diluted from 1:20 to 1:30 with water, $L_{conc}$ is less than $(1.9 - 0.4 \times Ca_{ready})$ M, where when the first concentrate is diluted from 1:20 to 1:40 with water and $Ca_{ready}$ ranges from 1.0 to 2.2 millimoles per litre.

19. The method of claim 18, wherein $L_{conc}$ is less than 1.4 M.

* * * * *